United States Patent [19]

Adhikary

[11] Patent Number: 4,863,930

[45] Date of Patent: Sep. 5, 1989

[54] USE OF SUBSTITUTED 5H-PYRIDO- AND 5H-THIAZOLO(2',1':2,3)IMIDAZO (4,5-B)INDOLES AS CHOLINOMIMETIC AGENTS

[76] Inventor: Parimal K. Adhikary, 1202 Davidson Rd., Nashville, Tenn. 37205

[21] Appl. No.: 943,345

[22] Filed: Dec. 19, 1986

[51] Int. Cl.$^4$ .................... A61K 31/44; A61K 31/425
[52] U.S. Cl. ..................................... 514/287; 514/366
[58] Field of Search ............................... 514/366, 287

[56] References Cited

PUBLICATIONS

K. L. Davis et al., *Cholinergic Drugs in Alzheimer's Disease*, Editorials, The New England J. of Med., vol. 315, No. 20, pp. 1286–1287 (1986).

J. H. Growdon et al., *Neurochemical Approaches to the Treatment of Senile Dementia*, Psychopathology in the Aged, pp. 281–294 (1980).

P. Davies, *Theoretical Treatment Posibilities for Dementia of the Alzheimer Type: The Cholinergic Hypythesis*, Theoretical Treatment Strategies for the Development of an Effective Treatment for Senile Dementia, pp. 19–32 (1981).

*Primary Examiner*—Douglas W. Robinson
*Assistant Examiner*—Richard Kearse

[57] ABSTRACT

5H-pyrido[2',1':2,3]imidazo[4,5-b]indoles of the formulae

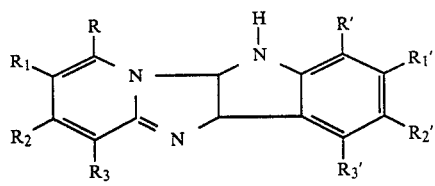

and

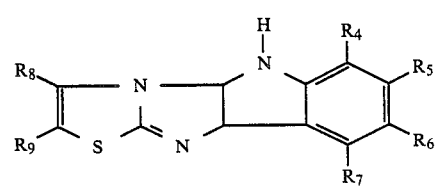

their pharmaceutically acceptable acid addition salts and the corresponding compounds bearing one or more halogens and/or lower-alkyl groups on the available ring carbon atoms are administered in cholinomimetic amounts to mammals with low acetylcholine or cholinergic activity to ameliorate the symptoms associated with that condition.

11 Claims, No Drawings

USE OF SUBSTITUTED 5H-PYRIDO- AND 5H-THIAZOLO(2',1':2,3)IMIDAZO (4,5-B)INDOLES AS CHOLINOMIMETIC AGENTS

BACKGROUND OF THE INVENTION

1. Field of the Invention

This invention relates to the use of known substituted 5H-pyrido[2',1':2,3] and 5H-thiazolo[2'3':2,3]imidazo[4,5-b]indoles as cholinomimetic agents.

2. Description of the Prior Art

My prior art U.S. Pat. Nos. 4,143,142, 4,160,840 and 4,204,067, whose disclosures are incorporated herein by reference, relate to substituted 5H-pyrido- and 5H-thiazolo[2',1':2,3]imidazo[4,5-b]indoles, to pharmaceutical compositions comprising them and to their use as antihypertensive agents in mammals. These compounds and others are employed in the method of this invention as cholinomimetic agents Cholinomimetic agents, e.g., tetrahydroaminoacridine and physostigmine, have shown considerable promise in delaying and to some extent reversing the deterioration of the mental processes, especially memory loss, associated with hypocholinergic patients in a neurogenic abnormal state, e.g., Alzheimer's disease. See Editorial, New Eng. J. of Med. 315 (20) 1286-7 (Nov. 13, 1986) and references cited therein; Summers et al., ibid., pp. 1241-5. See also Bartus et al., Annals of N.Y. Acad. Sci., 444, 332–358 (1985), which describes a method of measuring cholinergic deficiency in test animals For a review on the subject of the relationship of cholinergic activity of the caudate nucleus to memory, see Prado-Alcala, R.A., Life Sciences, 37, 2135-2142 (1985). See also Weingartner, H., Annals of N.Y. Acad of Sci., 444, 359-369 (1985) and Gamzu, E., ibid., 370-393 (1985).

SUMMARY OF THE INVENTION

This invention relates to methods of using 5H-pyrido[2',1':2,3] and 5H-thiazolo[2',3':2,3]imidazo[4,5-b]indoles as cholinomimetic agents in mammals, for example, humans and valuable warm-blooded animals such as laboratory rats, dogs, cats and other domestic animals in a neurogenic abnormal state by administering systemically thereto a cholinomimetic amount of a 5H-pyrido[2',1',2,3]imidazo[4,5-b]indole having one of the formulae

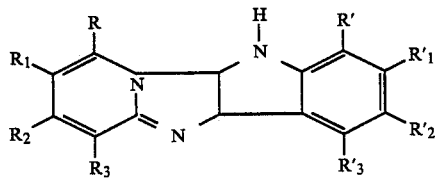

Ia and

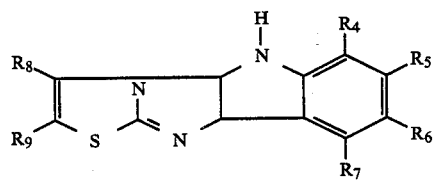

Ib or a pharmaceutically acceptable acid addition salt thereof, wherein R, R', $R_1$, $R'_1$, $R_2$, $R'_2$, $R_3$, $R'_3$, $R_4$, $R_5$, $R_6$ and $R_7$ each are hydrogen, halogen or lower-alkyl of from one to four carbon atoms, inclusive; $R_8$ is hydrogen or lower-alkyl of from one to four carbon atoms, inclusive; and $R_9$ is hydrogen or halo; preferably those of Formula Ia wherein R, $R_1$, $R_2$ and $R_3$ taken together constitute the following substituents on the tetracyclic ring: 10-halo, 8,10-dihalo, 8,9-di-lower-alkyl or 7,9-di-lower-alkyl and R', $R'_1$, $R'_2$, and $R'_3$ when taken together constitute the following substituents on the tetracyclic ring: 1-halo, 2-halo, 3-halo, 4-halo, 1-lower-alkyl, 2-lower-alkyl, 3-lower-alkyl, 4-lower-alkyl, 1,3-dihalo, 2,3-dihalo, 2,4-dihalo, 3,4-dihalo, 1,3-di-lower-alkyl, 2,3-di-loweralkyl or 1,4-di-lower-alkyl; and preferably those of Formula Ib wherein $R_4$, $R_5$, $R_6$, and $R_7$ when taken together constitute the following substituents on the tetracyclic ring: 9-halo, 8-halo, 7-halo, 6-halo, 9-lower-alkyl, 8-lower-alkyl, 7-lower-alkyl, 6-lower-alkyl, 7,9-dihalo, 7,8-dihalo, 6,8-dihalo, 6,7-dihalo, 7,9-di-lower-alkyl, 7,8-di-lower-alkyl or 4,6-di-lower-alkyl.

In the foregoing designation of variables, lower-alkyl means methyl, ethyl, propyl, isopropyl, butyl and the isomeric forms thereof, and halo means chloro, bromo, iodo and fluoro.

DETAILED DESCRIPTION OF THE INVENTION

As disclosed in the above-cited patents, most of the compounds of Formulae Ia and Ib are prepared by the phosphite reduction of the corresponding nitroso compounds. The reduction of a nitroso compound by triethylphosphite is described by J. I. Cadogan, Synthesis, 1, II (1972). The nitroso intermediates of pyridine and thiazole are prepared by condensation of an α-haloacetophenone respectively with 2-aminopyridine and 2-aminothiazole as described by Almirante et al., Journal of Medicinal Chemistry, 8, 305 (1968); ibid., 9, 29 (1966), and then nitrosation of the resulting base with sodium nitrite and acetic acid as described by La Rocca et al., Journal of Pharmaceutical Sciences, 60, 74 (1971).

The preferred method of recovering the imidazoindoles from the phosphite reduction mixture is to let the mixture solidify (about 24 hours required), wash with carbon tetrachloride on a glass filter and recrystallize the residue two times from 2-propanol.

The imidazoindoles may also be recovered from the phosphite reduction mixture by allowing it to solidify, washing the solid on a glass filter with cold carbon tetrachloride, taking the residue in a small quantity of chloroform, and eluating it over a column of activated alumina (80–325 mash). The first colored zone is mesh collected, evaporated to dryness and then recrystallized once from 2-propanol.

For the synthesis of most of the imidazoindole derivatives of my invention, known phenacyl halides or their ring substituted derivatives are used for condensation respectively with 2-aminopyridines or 2-aminothiazoles. In those isolated cases where a phenacyl halide with a desired halogen substitution in the ring is not readily available, the desired substitution in the phenyl ring is accomplished by first synthesizing the respective tetracyclic compound without the phenyl ring substituent and later introducing the desired substituent by halogenation. For example, meta-halo-phenacyl halides are not readily available. Therefore, the synthesis of 4-halo-5H-pyrido[2',1':2,3]imidazo[4,5-b]indoles or 6-halo-5H-thiazolo[2',3':2,3]imidazo[4,5-b]indoles is achieved by subsequent halogenation of the respective unsubstituted tetracyclic imidazoindole derivatives.

When a pyridine derivative is produced, the phosphite reduction is complete within 15-30 minutes of refluxing. Further heating yields gradual decomposition of this derivative. The thiazole derivative, Formula Ib, does not degrade upon prolonged heating during the reduction step.

Pharmaceutically acceptable acid addition salts of the compounds of Formulae Ia and Ib are prepared by reacting a compound of Formula Ia or Ib in free base form with a stoichiometric amount of an acid, such as hydrogen chloride, hydrogen bromide, hydrogen iodide, sulfuric acid, phosphoric acid, acetic acid, lactic acid, citric acid, succinic acid, benzoic acid, salicylic acid, pamoic acid, cyclohexanesulfamic acid, and the like.

The compounds of Formulae Ia and Ib are ordinarily administered in a pharmaceutical dosage unit form adapted for systemic administration (oral or parenteral administration). The term "dosage unit form" as used in this specification and in the claims refers to physically discrete units suitable as unitary dosages for mammalian subjects, each unit containing a predetermined quantity of the essential active ingredient, i.e., a compound of Formula Ia or Ib or a pharmaceutically acceptable acid addition salt thereof, calculated to produce the desired effect in combination with the required pharmaceutical means which adapt the said ingredient for systemic administration. Examples of dosage unit forms in accordance with this invention are tablets, capsules, orally administered liquid preparations in liquid vehicles, sterile preparations in liquid vehicles for intramuscular and intravenous administration, suppositories, and sterile dry preparations for the extemporaneous preparation of sterile injectable preparations in a liquid vehicle. Solid diluents or carriers for the solid oral pharmaceutical dosage unit forms are selected from the group consisting of lipids, carbohydrates, proteins and mineral solids, for example, starch, sucrose, kaolin, dicalcium phosphate, gelatin, acacia, corn syrup, corn starch, talc and the like. Capsules, both hard and soft, are formulated with conventional diluents and excipients, for example, edible oils, talc, calcium carbonate, calcium stearate and the like. Liquid preparations for oral administration are prepared in water or aqueous vehicles which advantageously contain suspending agents, such as, for example, ethanol, sodium carboxymethylcellulose, acacia, polyvinyl pyrrolidone, polyvinyl alcohol and the like. In the instance of injectable forms, they must be sterile and must be fluid to the extent that easy syringeability exists. Such preparations must be stable under the conditions of manufacture and storage, and ordinarily contain, in addition to the basic solvent or suspending liquid, preservatives in the nature of bactericidal and fungicidal agents, for example, parabens, chlorobutanol, benzyl, alcohol, phenol, thimerosal, and the like. In many cases, it is preferable to include isotonic agents, for example, sugars or sodium chloride. Carriers and vehicles include vegetable oils, ethanol and polyols, for example, glycerol, propylene glycol, liquid polyethylene glycol, and the like. Any solid preparations for subsequent extemporaneous preparation of sterile injectable preparations are sterilized, preferably by exposure to a sterilizing gas, such as, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general descriptions to provide from about 10 mg. to about 100 mg. of the essential active ingredient per dosage unit form. The amount of the essential active ingredient provided in the pharmaceutical dosage unit forms is based on my finding that the effective amount of compounds of the invention and acid addition salts thereof for obtaining a cholinomimetic effect in mammals is within a range from about 10 mg. per kg. to about 100 mg. per kg. of body weight of the recipient, daily, the higher dosages being required when administered orally or anally and the lower amounts being required by the intramuscular, intraperitoneal and intravenous routes.

Contemplated equivalents of this invention are methods of achieving a cholinomimetic effect in mammals employing a compound otherwise corresponding to Formula Ia or Ib, or a pharmaceutically acceptable acid addition salt thereof, but possessing another substituent instead of a lower-alkyl or halo group on the benzene, pyridine or thiazole ring, e.g., trifluoromethyl or a higher alkyl group, e.g., amyl or hexyl, and which possess cholinergic activity comparable to the compounds employed in this invention.

The method of this invention is useful in ameliorating the symptoms of a number of neurogenic diseases and disorders associated with a cholinergic deficit, e.g., Alzheimer's disease, Huntington's disease, myesthenia gravis, muscular dystrophy, and especially the memory loss often associated therewith Cholinergic deficit, due either to insufficient acetylcholine production or to excessive cholinerase activity is believed to be the or a causative factor for these diseases/disorders. By correcting acetylcholine deficiency and/or cholinergic response of the effector organs, the disturbing symptoms associated with such diseases are ameliorated and diminished, even when the ultimate course of the disease is not altered. In in vitro assays, the compounds of Formulae Ia and Ib and their pharmaceutically acceptable acid addition salts are bioactive at concentrations as low as $10^9$ M and are generally nontoxic at dosage levels of about 100 mg./kg. body weight.

A compound of Formula Ia or Ib or a pharmaceutically acceptable acid addition salt thereof is ordinarily administered at least daily, e.g., once every 4-24 hours, on a plurality of successive days, e.g., 7-365 or more, until a favorable response is noted and for as long as the compound is tolerated by the patient. Individual response will vary and therefore some adjustment of dosage may be required to minimize side effects or maximize the favorable response. Generally, plasma levels of about 2 $\mu$g/ml to about 10 $\mu$g./ml. give the best results. As in the case of THA, although a cure of diseases such as Alzheimer's may not be achieved, a favorable palliative effect on the mentally debilitating symptoms of the disease can be achieved for prolonged periods of time.

The synthesis and antihypertensive activities of the unsubstituted compounds of Formulae Ia and Ib, i.e., wherein $R'$, $R'_1$, $R'_2$, $R'_3$, $R$, $R_1$, $R_2$ and $R_3$ are H (Comp. 1) and $R_4$-$R_9$ are H (Comp. 2) have been reported. See Adhikary et al., J. Med. Chem., 19, 1352 (1976); prevention of cardionephric damages in spontaneous hypertensive rats (SHR) by chronic administration of Comp. 1 have also been reported. See Adhikary et al., AAAS Annual Meeting Abstracts, #304, 26-31, May 1985, Los Angeles.

Pharmacology and Cholinomimetic Effects

The two compounds were investigated for their effects on the cholinergic system in the frog, rat, guinea pig and rabbit. Comp. 1 reversibly potentiated the neurally evoked twitch tension in the frog sciatic nerve - sartorius preparations. .It did not produce any contracture or alter the directly elicited twitches Comp. 1 increased the endplate and miniature endplate potentials, and quantal contents in the frog sartorius muscles. Comp. 1 increased the spontaneous motility of guinea pig ileum and decreased the heart rate. However, in the presence of antimuscarinic agent, atropine, Comp. 1 failed to potentiate the motility of ileum and slow the heart rate. Comp. 1 increased acetylcholine-induced contracture in the rat vas deferens but its effect was attenuated by atropine In the denervated preparation, this compound also potentiated the acetylcholine-induced contracture.

Comp. 2 potentiated the neurally evoked twitches in the frog muscle, acetylcholine-induced contracture in the denervated rat soleus and slowed the heart rate in the rabbit.

Thus, the effects of these two imidazole compounds on different preparations strongly suggest that they interact with both nicotinic and muscarinic acetylcholine receptors and release acetylcholine from the presynaptic nerve terminals.

Effects on Twitch Tension of the Frog Sartorius Muscle

In this test, Comp. 1 potentiated the indirectly elicited twitch without affecting the directly elicited twitch. The effect of 50 $\mu$M Comp. 1, which potentiated the neurally evoked twitches by 15% in about 10 min., was small but concentration-dependent. There was no change in the directly evoked twitches Comp. 2 also produced a similar effect on neurally evoked twitches Washing the muscle with Ringer's solution for 60 min. resulted in complete recovery of the neurally evoked twitches.

Effects on Resting Membrane Potential and Quantal Content Of the Frog Sartorius Muscle At concentrations varying from 1 $\mu$M to 50 $\mu$M, Comp. 1 did not significantly change the membrane potential of the junctional and extrajunctional region of surface fibers (control, 82±2.0 mV; Comp. 1 (50 M), 81±2.2 mV. Comp. 1 ( $\mu$M) increased the miniature endplate potentials by 96% and quantal content by 95% in the sciatic nerve-sartorius muscle preparations.

Effects on Spontaneous Motility of Guinea Pig Ileum

Comp. 1 increased the spontaneous motility of guinea pig ileum in a concentration-dependent manner. At 10 and 100 $\mu$M concentration, Comp. 1 potentiated the motility to 200 and 375% of control, respectively. However, Comp. 1 failed to induce contractility in the presence of 1 $\mu$M atropine. Comp. 2 also produced similar effect on guinea pig ileum.

Effect on Rat Vas Deferens

At 1-100 $\mu$M, Comp. 1 did not induce contraction in the nonsimulated rat vas deferens. However, Comp. 1 potentiated the acetylcholine-induced contractions of the vas deferens. In the presence of atropine (1 $\mu$M), Comp. 1 response on acetylcholine-induced contraction was inhibited.

Effect on Denervated Rat Soleus Muscle

At 1-100 $\mu$M, Comp. 1 itself did not produce any contracture in the denervated rat soleus. However, Comp. 1 increased the acetylcholine-induced contracture. Comp. 2 also showed similar effect on acetylcholine-induced contracture of denervated rat soleus muscle.

Effects on Isolated Rabbit Heart

Comp. 1 decreased the heart rate and slightly increased the myocardial contractility of the isolated rabbit heart in a concentration-dependent manner. The heart rate was decreased by 10-20% and the myocardial contractility was increased by 2-7% at 0.01 to 1.0 $\mu$M, respectively. At higher concentration, Comp. 1 had less inhibitory effect on heart rate and myocardial contractility. Comp. 2 had similar effects on heart rate but no effect on myocardial contractility.

Studies demonstrate that Comps. 1 and 2 mimic cholinergic activity in the frog, rat, guinea pig and rabbit at the concentrations used. These compounds act upon nicotinic and muscarinic acetylcholine receptors at both pre- and postsynaptic sites These conclusions are based upon he following actions of these agents: Comp. 1 (a) potentiates neurally evoked twitches without affecting the direct twitches; (b) potentiates acetylcholine-induced contracture in the denervated rat soleus; (c) reduces the amplitude of miniature endplate potentials and increases the quantal content; (d) accelerates the spontaneous motility of the guinea pig ileum and acetylcholine-induced contracture in the rat vas deferens; and slows the isolated rabbit heart.

These studies establish that Comp. 1 increases the indirectly elicited twitches in the frog sciatic nerve-sartorius preparations, indicating an acceleration of neuromuscular transmission. Since this compound increases the amplitude of the miniature endplate potentials and increases the quantal content without altering quantal size, the compound interacts at the presynaptic site and releases acetylcholine. The denervated rat soleus (5-7 days) lacks presynaptic nerve terminals and functional cholinesterase. Thus, potentiation of acetylcholine-induced contracture in the denervated rat soleus by Comp. 1 and Comp. 2 strongly suggests that they interact or sensitize the postsynaptic nicotinic acetylcholine receptors.

Activation of muscarinic acetylcholine receptors causes increased motility in the guinea pig ileum and potentiation of acetylcholine-induced contracture in the rat vas deferens. Similarly, activation of muscarinic receptors causes slowing of the heart rate in an isolated preparation of rabbit heart. Comp. 1 causes an increased motility of the guinea pig ileum, potentiation of acetylcholine-induced contracture in the vas deferens and slowing of the heart rate. Therefore, Comp. 1 sensitizes and/or interacts with muscarinic acetylcholine receptors in these preparations The results of these studies confirm that the compounds employed in this invention are cholinomimetics. They react with both nicotinic and muscarinic acetylcholine receptors and release acetylcholine from the presynaptic nerve terminals.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight, unless otherwise indicated.

EXAMPLES

Adult patients, who are clinically diagnosed as suffering from either Alzheimer's disease or from old-age-related memory loss are suitable candidates for therapeutic treatment with a compound of Formula Ia or Ib or a pharmaceutically acceptable acid addition salt thereof. The diagnostic criteria for Alzheimer's disease will be the same as referred to by Summers et al., N. Engl. J. Med. 315, 1241–5 (1986), and/or by identification of the protein A-68 in the patient's blood. The diagnostic procedure for old-age-related memory loss is the standard differential diagnosis, known as DSM-III. See The Diagnostic and Statistical Manual of Mental Disorders (3d ed.), or DSM-III, of the American Psychiatric Association, 1980; the report, "Senility Reconsidered," by a Task Force of the National Institute on Aging, 1980; the report, "Dementia," by the Council on Scientific Affairs of the American Medical Association, 1985; and the report, "Clinical Diagnosis of Alzheimer's Disease and Related Disorders Association," McKhann et al. 1984. Positive diagnosis of the dementia and recognition of memory dysfunction due to diminished in vivo cholinergic activity will facilitate therapeutic treatments with the cholinomimetic agents employed in this invention. After being positively diagnosed about causative factor(s) of his/her memory dysfunction, the patient will be treated therapeutically with Comp. 1 (pyridino-imidazoindole) or Comp. 2 (thiazolo-imidazoindole) or any of their derivatives in the following dose levels and administration procedures:

EXAMPLE 1

To an Alzheimer's disease patient suffering moderate memory loss (to minimize possible adverse reactions, patients with abnormal liver function or with obstructive pulmonary disease are excluded), administer 10 mg/day of pyridino(1,2-a)-imidazo(5,4-b)indole, per oral (p.o.) (approx. 2 μm/L of blood) or 5 mg/day, intramuscularly (i.m.), intravenously (i.v.) or subcutaneously (s.c.) (in saline solution) once a day for 30 consecutive days. If the medication is well tolerated, during the next 30 days double the medication by administering equal quantities two times a day. In the absence of any drug-related side effects, the medication level is increased five times during the third month of initial medication by administering the drug five times a day either 10 mg/each time, p.o. or 5 mg/each time, i.m., i.v. or s.c. (in saline solution). After the conclusion of the first 3 months of chemotherapy, the patient's condition (memory function) is then clinically evaluated. If progress is noted, medication is further continued at dose levels between 50 mg–100 mg/day, p.o. or 25 mg–50 mg/day; i.m., i.v. or s.c. for further period of time so long as the benefit of such medication is noticeable.

EXAMPLE 2

Follow the procedure of Example 1, except administer 5H-thiazolo(2',3':2,3)imidazo(5,4-b)indole. Comparable beneficial effects on memory function will be noted.

Following the procedure of Example 1 or Example 2, comparable results are obtained employing a molar equivalent amount of one of the following 5H-pyrido[2',1':2,3]imidazo[4,5-b]indoles and 5H-thiazolo[2',1':2,3]imidazo[4,5-b]indoles: 1-,2-,3-,4-,7-,8-, 9- and 10-methyl-, 1-,2-,3-,4-,7-,8-, 9- and 10-ethyl-, 1-,2-,3-,4-,7-,8-, 9- and 10-propyl-, 1-,2-,3-,4-,7-,8-, 9- and 10-isopropyl-, 1-,2-,3-,4-,7-,8-, 9- and 10-butyl-, 1-,2-,3-,4-,7-,8-, 9- and 10-sec-butyl-, 1-,2-,3-,4-,7-,8-, 9- and 10-chloro-, 1-,2-,3-,4-,7-,8-, 9- and 10-bromo-, 1-,2-,3-,4-,7-,8-, 9- and 10-fluoro-, 1-,2-,3-,4-,7-,8-, 9- and 10-iodo-, 1,3-,2,3-,2,4-,3,4- and 8,10-dichloro-, 1,3-,2,3-,2,4-,3,4- and 8,10-dibromo-, 1,7-,1,8-,1,9-,1,10-,2,4-,2,7-,2,8-,2,9-,2,10-,3,7-, 3,8-,3,9-,3,10-,4,7-,4,8-,4,9-,4,10-,7,9- and 8,9-dimethyl-, 7,9-diethyl-, 7,9-dipropyl-, 7,9-diisopropyl- and 7,9-di-n-butyl-, 8,9-diethyl-, 8,9-dipropyl- and 8,9-diisopropyl-, 10-chloro-4-methyl 10-bromo-4-methyl, 10-chloro-4-ethyl-, 10-chloro-4-butyl-, 10-chloro-4-propyl-, 10-chloro-2,4-dimethyl-, 10-chloro-2,4-diethyl-, 10-chloro-2,4-dipropyl-, 10-chloro-2,4-dibutyl-, 4,10-dichloro-, 4,10-dibromo-, 10-chloro-2,4-dichloro-, 10-bromo-2,4-dibromo-, 10-chloro-2,4-dibromo-, 10-bromo-2,4-dichloro-, 4-chloro-9-methyl-, 2,4-dichloro-9-methyl-, 2,4-dichloro-9-ethyl-, 2,4-dichloro-9-propyl-, 2,4-dichloro-9-butyl-, 2,4-dibromo-9-methyl-, 2,4-dibromo-9-ethyl-, 2,4-dibromo-9-propyl- and 2,4-dibromo-9-butyl-5H-pyrido[2',1':2,3]imidazo[4,5-b]indole and the correspondingly substituted 5H-thiazolo[2',1':2,3]imidazo[4,5-b]indoles bearing one or more halo and/or alkyl groups on the thiazole and/or benzene rings.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating a hypocholinergic mammal by ameliorating the symptoms associated with a cholinergic deficiency, which comprises administering a mammal in need thereof a therapeutically effective amount of a compound of one of the formulae

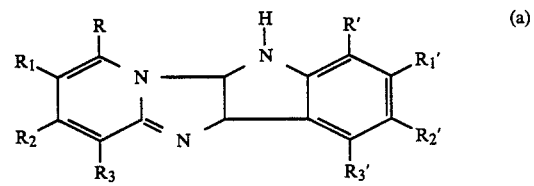

(a)

and

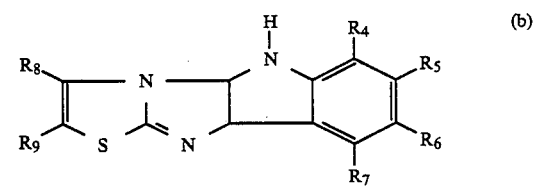

(b)

or a pharmaceutically acceptable acid addition salt thereof, wherein R, R', $R_1$, $R'_1$, $R_2$, $R'_2$, $R_3$, $R'_3$, $R_4$, $R_5$, $R_6$ and $R_7$ each are hydrogen, halogen or lower-alkyl of from one to four carbon atoms, inclusive; $R_8$ is hydrogen or lower-alkyl of from one to four carbon atoms, inclusive; and $R_9$ is hydrogen or halo.

2. The method according to claim 1, wherein the mammal is a human being.

3. The method according to claim 1, wherein the compound is administered by injection.

4. The method according to claim 1, wherein the compound administered is a compound of Formula Ia or a pharmaceutically acceptable salt thereof.

5. The method according to claim 4, wherein R, $R_1$, $R_2$ and $R_3$ collectively are 10-halo, 8,10-dihalo, 8,9-di-lower-alkyl or 7,9-di-lower-alkyl and R', $R'_1$, $R'_2$, and $R'_3$ collectively are 1-halo, 2-halo, 3-halo, 4-halo, 1-lower-alkyl, 2-lower-alkyl, 3-lower-alkyl, 4-lower-alkyl, 1,3-dihalo, 2,3-dihalo, 2,4-dihalo, 3,4-dihalo, 1,3-di-lower-alkyl, 2,3-di-lower-alkyl or 1,4-di-lower-alkyl.

6. The method according to claim 5, wherein the compound administered is 5H-pyrido[2',1':2,3]imidazo[4,5-b]indole or a pharmaceutically acceptable salt thereof.

7. The method according to claim 6, wherein the mammal is a human being and wherein the compound is administered by injection.

8. The method according to claim 1, wherein the compound administered is a compound of Formula Ib or a pharmaceutically acceptable salt thereof.

9. The method according to claim 8, wherein $R_4$, $R_5$, $R_6$, and $R_7$ collectively are 9-halo, 8-halo, 7-halo, 6-halo, 9-lower-alkyl, 8-lower-alkyl, 7-lower-alkyl, 6-lower-alkyl, 7,9-dihalo, 7,8-dihalo, 6,8-dihalo, 6,7-dihalo, 7,9-di-lower-alkyl, 7,8-di-lower-alkyl or 4,6-di-lower-alkyl.

10. The method according to claim 9, wherein the compound administered is 5H-thiazolo[2'1':2,3]imidazo[4,5-b]indole or a pharmaceutically acceptable salt thereof.

11. The method according to claim 10, wherein the mammal is a human being and wherein the compound is administered by injection.

* * * * *